(12) United States Patent
Velikaris et al.

(10) Patent No.: US 6,524,238 B2
(45) Date of Patent: Feb. 25, 2003

(54) UNIVERSAL HANDLE AND METHOD FOR USE

(75) Inventors: James Velikaris, Schwenksville, PA (US); Sean Kerr, Oreland, PA (US)

(73) Assignee: Synthes USA, Paoli, PA (US)

( * ) Notice: Subject to any disclaimer, the term of this patent is extended or adjusted under 35 U.S.C. 154(b) by 0 days.

(21) Appl. No.: 09/742,254

(22) Filed: Dec. 20, 2000

(65) Prior Publication Data

US 2002/0077530 A1 Jun. 20, 2002

(51) Int. Cl.$^7$ .................................................. A61B 1/32
(52) U.S. Cl. ............................ 600/213; 606/99; 16/422
(58) Field of Search .................... 606/1, 96, 99, 606/151; 81/489; 600/213, 226; 16/110.1, 111.1, 422

(56) References Cited

U.S. PATENT DOCUMENTS

| | | | |
|---|---|---|---|
| 4,608,972 A | 9/1986 | Small | 128/92 |
| 4,683,896 A | 8/1987 | Herbst et al. | 128/785 |
| 4,705,038 A | 11/1987 | Sjostrom et al. | 128/305 |
| 4,713,077 A | 12/1987 | Small | 623/16 |
| 5,147,367 A | 9/1992 | Ellis | 606/96 |
| 5,190,549 A | 3/1993 | Miller et al. | 606/85 |
| 5,224,930 A | 7/1993 | Spaeth et al. | 604/33 |
| 5,380,291 A | 1/1995 | Kaali | 604/164 |
| 5,445,641 A | 8/1995 | Frigg et al. | 606/86 |
| 5,507,801 A | 4/1996 | Gisin et al. | 606/86 |
| 5,586,991 A | 12/1996 | Yoon | 606/185 |
| 5,618,309 A | 4/1997 | Green et al. | 606/207 |
| 5,755,721 A | 5/1998 | Hearn | 606/96 |
| 5,807,338 A | 9/1998 | Smith et al. | 604/164 |
| 5,817,110 A | 10/1998 | Kronner | 606/148 |
| 5,843,039 A | 12/1998 | Klemm | 604/164 |
| 5,851,216 A | 12/1998 | Allen | 606/185 |
| 5,948,000 A | 9/1999 | Larsen et al. | 606/232 |
| 5,951,561 A | 9/1999 | Pepper et al. | 606/80 |
| 5,957,927 A | 9/1999 | Magee et al. | 606/99 |
| 5,957,947 A | 9/1999 | Wattiez et al. | 606/185 |
| 5,980,493 A | 11/1999 | Smith et al. | 604/164 |
| 5,984,865 A | 11/1999 | Farley et al. | 600/213 |
| 5,993,470 A | 11/1999 | Yoon | 606/185 |
| 6,004,326 A | 12/1999 | Casto et al. | 606/99 |
| 6,013,083 A | 1/2000 | Bennett | 606/104 |

FOREIGN PATENT DOCUMENTS

| | | |
|---|---|---|
| DE | 1 034 322 | 7/1956 |
| DE | 44 16976 A1 | 11/1995 |
| DE | 298 09 038 U1 | 9/1998 |

OTHER PUBLICATIONS

Leibinger catalog excerpt, pp. 10–11, trocar and drill guide.

Primary Examiner—Kevin Shaver
Assistant Examiner—Michael B. Priddy
(74) Attorney, Agent, or Firm—Pennie & Edmonds LLP

(57) ABSTRACT

The present invention provides an improved handle which may be used to releaseably hold various types of surgical instruments employed in medical or dental procedures. The handle is comprised of a grasping portion and a lock assembly that contains a retractable slider pin designed to engage one or more indentations provided with instruments intended for use with the handle. The lock assembly may be provided with at least one biasing member which holds the pin in an extended position thereby locking the surgical instrument to the handle. The instrument may be removed from the handle or rotated by the user retracting the pin to release the instrument from the handle. A system and a method of interchangeably using surgical instruments in the handle is also disclosed.

59 Claims, 9 Drawing Sheets

UNIVERSAL HANDLE AND METHOD FOR USE

BACKGROUND OF THE INVENTION

The present invention generally relates to surgical instruments used in surgical procedures, and more particularly to an improved handle that permits various instruments to be releaseably attached for quicker and easier interchange.

The development of newer minimally invasive surgical techniques, such as laparoscopic surgery, have allowed surgeons to successfully perform numerous operative procedures in many instances which in the past required the need for large surgical incisions. In this newer procedure, one or several very small incisions are made in the patient through which various surgical instruments may be used to perform the required surgical procedure. Minimally invasive surgery offers benefits which include creating less trauma to the patient, reducing the risk of post-operative infections, and allowing speedier recovery than conventional surgery with its larger incisions.

Trocars are commonly used in minimally invasive surgeries. They generally consist of a hollow cannula (tube) and an obturator (bladed or pointed piercing device) which are used, in combination, to make a small portal into a patient. The obturator is designed to slide inside the cannula to create a single unit that may be used to penetrate a small incision that has been previously made by a surgeon. Once the trocar has penetrated the patient's body cavity, the obturator is withdrawn while leaving the cannula in position. Various surgical instruments can then be worked through the cannula to perform whatever surgical technique is required.

Trocars are particularly useful in many types of surgery in which a small incision will permit the required surgical procedure to be completed. One such application is in maxillofacial surgery where bone fractures occurring in the maxilla or mandible are stabilized by bone screws and/or bone plates. In this trocar application, drill guides can be inserted through the cannula which allow the surgeon to pre-drill holes in the bone for receiving bone screws. Trocars can also be used with soft tissue retractors, such as cheek retractors which are employed to hold the tissue away from the surgical site so that it does not interfere with fixation of the facial fracture.

The cannula may be fastened or secured to a handle of some type. This helps the surgeon control the trocar and facilitates the process of both making the initial incision accurately and subsequently working with various instruments in a manner which reduces the chance of the cannula being pulled from the patient's body cavity prematurely.

Handles of the past have typically employed various approaches for coupling the cannula to the handle. For example, cannulas were often attached in a permanent manner to the handle such as by welding. Semi-permanent type couplings have also been used such as threading the cannula head to the handle, or providing set screws to hold both parts together. U.S. Pat. No. 5,755,721 to Hearn discloses another semi-permanent type of coupling wherein a retaining ring with an internal depression around its circumference is provided that mates with a spring and ball detent on a surgical instrument. The instrument is pushed into the retaining ring until the detent is seated in the depression.

The handle designs of the past have several drawbacks. The permanent type attachment does not allow the surgeon to interchange different kinds or sizes of surgical instruments. This reduced flexibility for the surgeon and increased prices for each trocar unit which must contain both a handle and permanently affixed cannula. Overall inventory costs are thereby also increased.

Although the semi-permanent type couplings offer interchangeability of surgical instruments, they too have been problematic. Using set screws or threaded coupling of the cannula to the handle makes changing instruments cumbersome, especially when it must be done during the exigencies of a surgical procedure. While offering improvement, the coupling described in the Hearn patent does not positively lock the cannula to the handle in a manner that requires the surgeon to unlock the cannula from the handle.

Accordingly, there is a need for a handle which allows for improved releasability and interchangeability of various surgical instruments with the handle while overcoming the problems associated with the foregoing prior art devices.

BRIEF SUMMARY OF THE INVENTION

The invention is generally directed to a handle and system of surgical tools which can be designed specifically to be compatible and interchangeable with the handle.

In accordance with one embodiment, the handle is comprised of a grasping portion and a handle lock assembly. The grasping portion is used by the surgeon to hold and control the handle. The handle lock assembly comprises a body with a top and a bottom, and further includes a retractable slider pin which secures a surgical instrument to the handle.

In another embodiment, the lock assembly body includes an opening disposed in the body through which surgical instruments are inserted. The opening, which is preferably circular in one embodiment, extends from the top to the bottom of the lock assembly body creating an opening passing completely through the body. The retractable slider pin is movable from an extended position in which the pin protrudes into the opening and secures the surgical instrument to the handle, to a retracted position in which the pin is withdrawn from the opening.

The slider pin may be connected to a handle slider which is preferably a rectangular or square block in configuration, but is not limited to those shapes. The slider pin may be integrally connected with the handle slider such as by welding or the slider pin and handle slider may be formed as an integral unit. Also preferably, the handle slider is slidably mounted in a cavity or other opening provided in the body of the handle lock assembly. Alternatively, the handle slider may be mounted on the exterior of the handle lock assembly which is a matter of design choice.

In one embodiment, the handle lock assembly of the handle includes at least one handle release. The handle release is used to move the retractable slider pin from the extended position to the retracted position as discussed above. The handle release is connected to the handle slider which is connected to the slider pin, thereby moving the pin.

In accordance with another embodiment, at least one biasing member is provided which biases the slider pin toward its extended position. Preferably, the biasing member is a helical spring. In one embodiment, the biasing member may be held by a recess provided in the handle slider. The handle lock assembly may be attached to the grasping portion of the handle by welding. The handle including the grasping portion and handle lock assembly may be made of stainless steel, however, it may be made of any material suitable for the intended application. The grasping portion of the handle may be hollow which reduces the cost and weight of the handle.

In accordance with one embodiment, the surgical instrument that may be used with the handle of the invention is a cannula or trocar assembly. The cannula, or different instrument as the case may be, may include indentations which are designed to engage the retractable slider pin thereby securing the cannula to the handle. Preferably, the cannula or different instrument may further include additional depressions which may be used to secure at least one additional surgical device to the handle. In one embodiment, a soft tissue retractor is an additional device that may be attached to the handle. Preferably, the cannula or different instrument, and additional devices that may be attached to the handle may be made of stainless steel, however, they may be made of any material suitable for the intended application. The cannula or different instrument may further include a body portion and a head portion, and preferably where these two portions are of different size diameters, an inclined ramp may be included between the two portions to facilitate insertion of the cannula into the handle as discussed below. The cannula or different surgical instrument may further comprise a knob connected to the cannula or different instrument for grasping and rotating the cannula or different instrument. At least one slot may be provided in the knob for mating and engaging with at least one tab provided on a surgical instrument intended to be inserted through the cannula or different surgical instrument secured to the handle to prevent rotation of the inserted instrument in the cannula or different instrument. An obturator or a drill guide which are well known in the art may be such an instrument provided with at least one tab which mates with the at least one slot in the knob of the cannula or different instrument.

In another embodiment, the handle lock assembly body of the handle may include a transition portion between the handle lock assembly and the grasping portion. The grasping portion preferably may be angularly displaced, preferably about 30 degrees, from the plane of the top of the handle lock assembly.

A handle lock system for performing a surgical procedure is also provided. The system may comprise a handle which has a grasping portion and handle lock assembly. The lock assembly comprises a body with a top and a bottom, and a retractable slider pin. The system further may include a cannula or different instrument having indentations to engage the slider pin thereby securing the cannula to the handle. In one embodiment, the handle lock system may further include additional depressions for securing an additional surgical instrument to the trocar handle. Preferably, the additional surgical instrument may be a soft tissue retractor.

A method of interchangeably using surgical instruments in a handle lock assembly, and a trocar specifically, is also provided, which may comprise the steps of: (a) providing a handle, the handle having a grasping portion and a lock assembly, the lock assembly comprising a body with a top and a bottom, a retractable slider pin, and a passageway disposed in the body wherein the surgical instruments are inserted for securing to the handle, the retractable slider pin being movable from an extended position in which the pin protrudes into the passageway to a retracted position in which the pin is withdrawn from the passageway; (b) providing a cannula having indentations to engage the retractable slider pin thereby securing the cannula to the handle; (c) inserting the cannula in the handle; (d) locking the cannula to the handle by engaging the retractable pin in one of the indentations; (e) retracting the retractable pin from the extended position to the retracted position; and (f) removing the cannula from the handle. The method may comprise inserting a different surgical instrument having indentations into the passageway other than a cannula. The method may further include inserting an obturator into the cannula.

In another embodiment of the method, locking the cannula or different surgical instrument to the handle may further include the steps of withdrawing the slider pin from the passageway to the retracted position by a user and inserting the cannula or different instrument into the passageway before the slider pin engages one of the indentations. The method may also further include the step of rotating the cannula or different instrument to align the indentations and sliding pin to lock the cannula or different instrument to the handle.

It will be appreciated by one skilled in the art that the invention is particularly useful for maxillofacial surgical procedures. However, use of the invention is not limited to maxillofacial surgery alone and the invention may be used with and in any type of medical or dental procedure where it is desirable to releaseably attach medical or dental instruments to a handle.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE INVENTION

Figure 1:
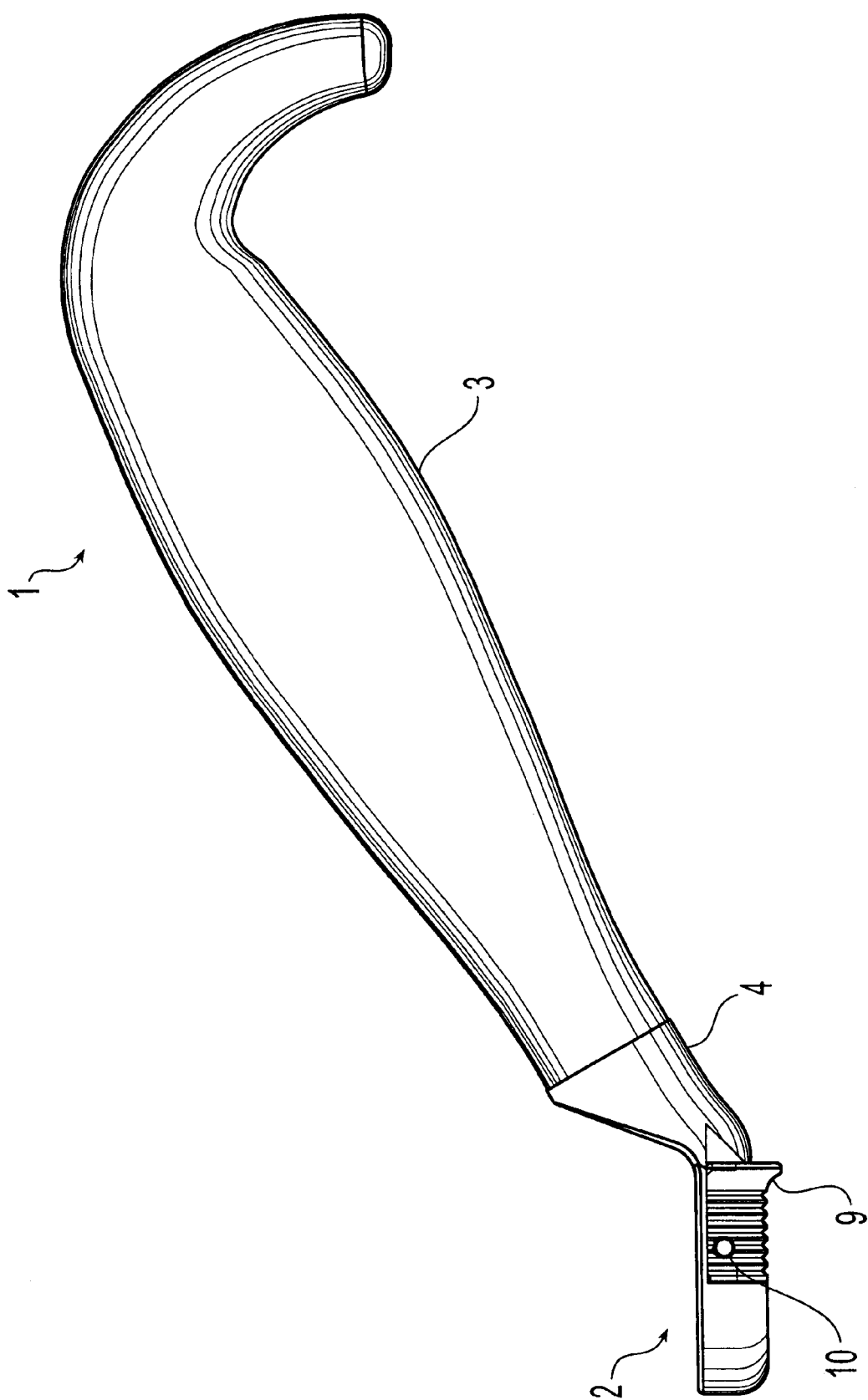
FIG. 1 is a side elevation view of the handle of the present invention.

Referring to FIG. 1, the handle 1 is depicted in one embodiment as including a handle lock assembly 2 and a grasping portion 3. Handle lock assembly 2 may include a transition portion 4 connected to grasping portion 3 as shown; however, lock assembly 2 may be attached directly to grasping portion 3 with minimal or no transition depending on the shape and design of the handle 1 desired. It will further be readily apparent that the shape of the grasping portion 3 is a matter of ergonomic design choice and is not limited to the embodiment shown. Furthermore, grasping portion 3 may be formed of one or more pieces secured together in any manner commonly used in the art (e.g., welding, set screws, etc.) and may be either solid or hollow. It will also be appreciated that the size, shape, and position of the lock assembly 2 on the grasping portion 3 is a matter of design choice and is similarly not limited to the preferred embodiment shown.

Figure 2A:
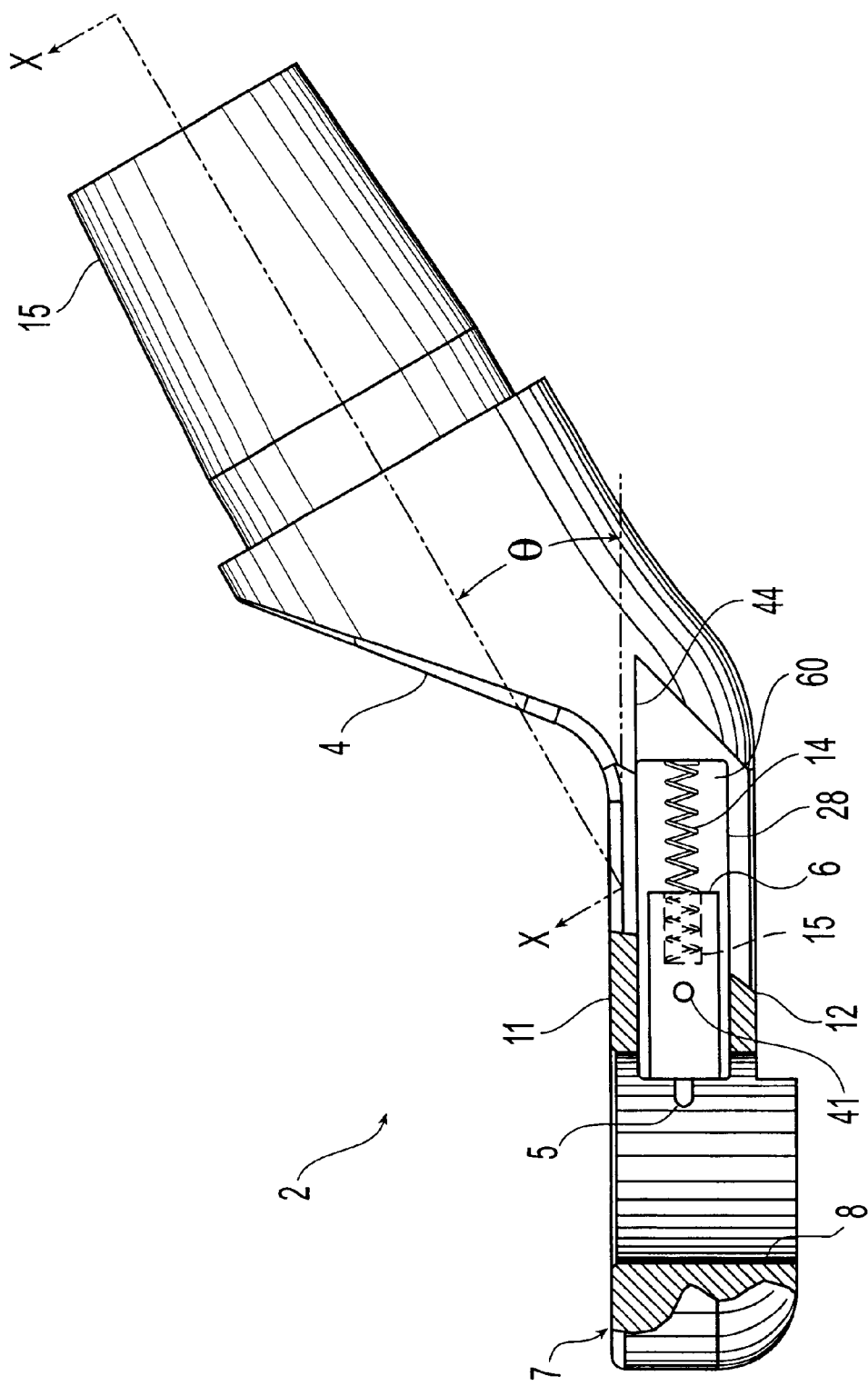
FIG. 2A is a side elevation view of the handle lock assembly of the handle of FIG. 1 shown with the handle release removed.
Figure 2B:
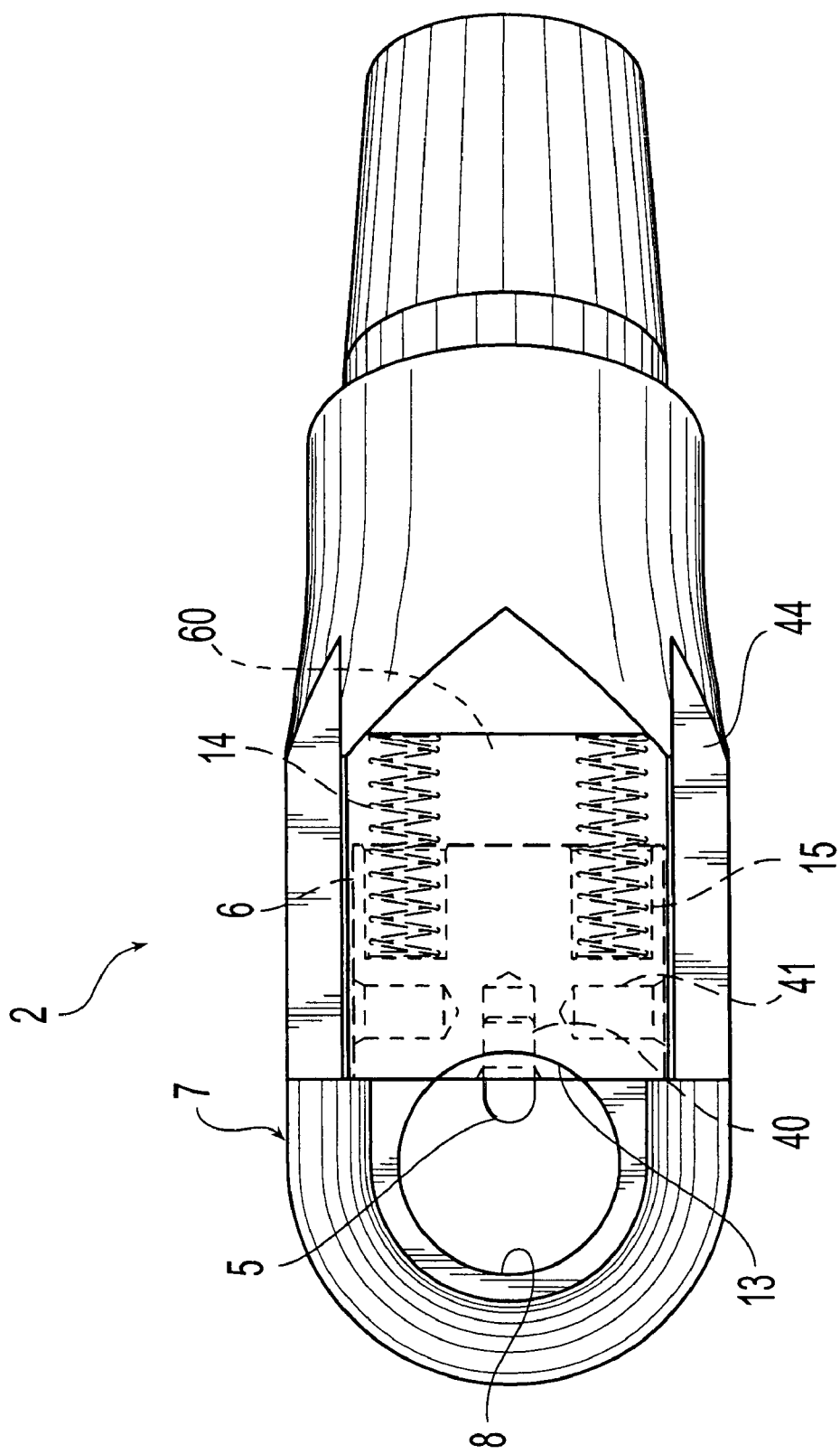
FIG. 2B is a bottom plan view of the handle lock assembly of the handle of FIG. 1 shown with the handle release removed.
Figure 2C:
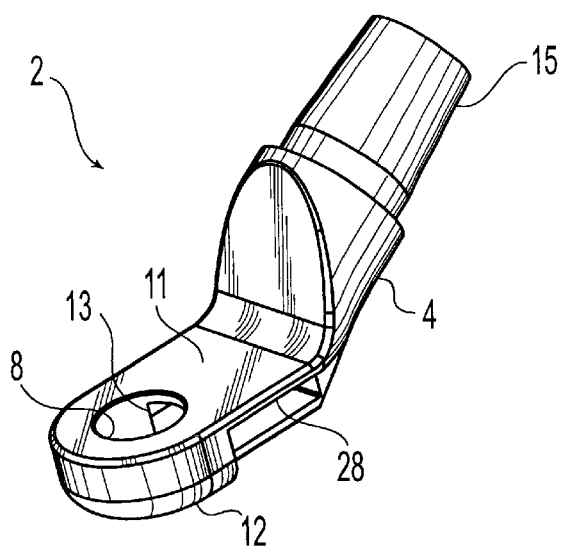
FIG. 2C is an isometric view of the handle lock assembly of the handle of FIG. 1 shown with the handle release removed.
Figure 2D:
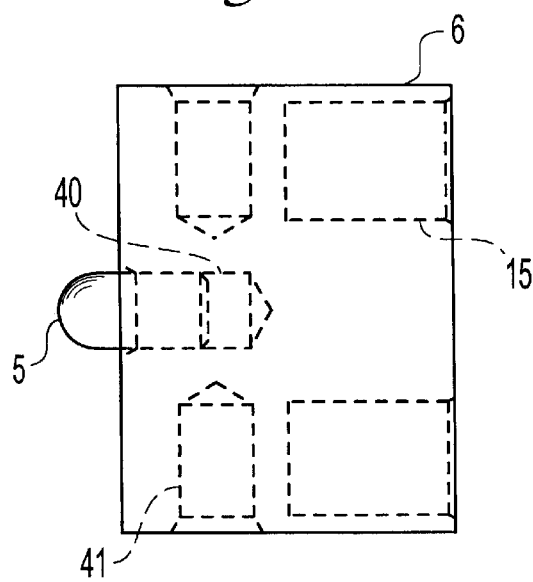
FIG. 2D is a plan view of the handle slider of the handle lock assembly of the handle of FIG.1.
Figure 2E:
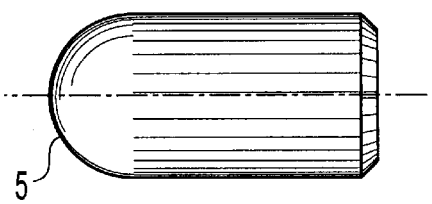
FIG. 2E is a view of the slider pin of the handle lock assembly of the handle of FIG. 1

FIGS. 2A–2G depict the handle lock assembly 2 of the handle 1 in more detail (for clarity, the same numerical designations are used for same parts in every figure contained herein). Referring to FIG. 2A, the handle lock assembly 2 comprises a body 7, a retractable slider pin 5, and a handle slider 6 which is slidably mounted within a cavity 60 provided in body 7. Preferably, handle slider 6 is a rectangular or square block in which various recesses have been made to accommodate other components of the handle lock assembly 2 (best seen in FIG. 2D). Pin 5 (FIG. 2E) is rigidly connected to handle slider 6, preferably by press fitting the pin into recess 40 provided in slider 6 (FIG. 2D). Alternatively, the pin 5 may be attached to the handle slider 6 in any manner commonly known in the art, and may in fact be an integral part of the slider 6 formed during manufacture of the slider. Pin 5 as shown preferably has rounded edges to facilitate engaging the indentations provided in surgical instruments as will be described below.

Figure 2F:
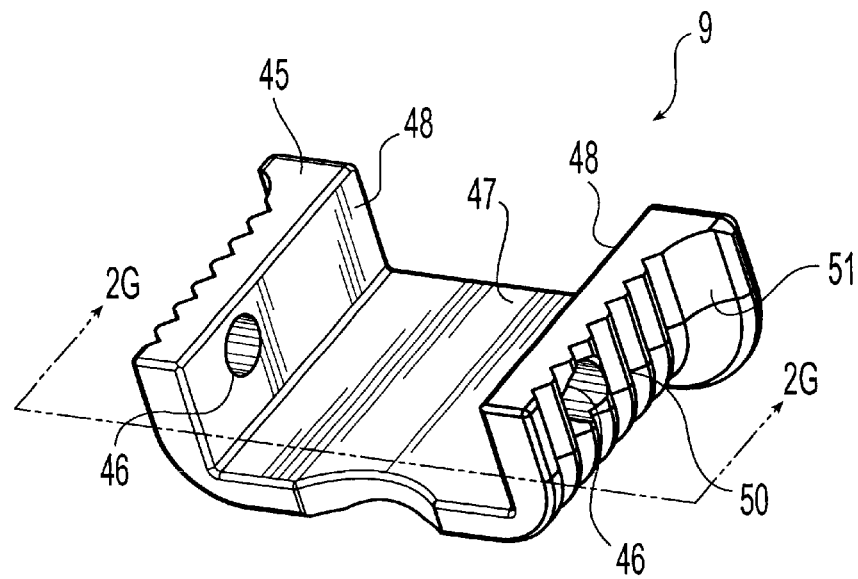
FIG. 2F is an isometric view of the handle release of the handle lock assembly of the handle of FIG. 1.
Figure 2G:
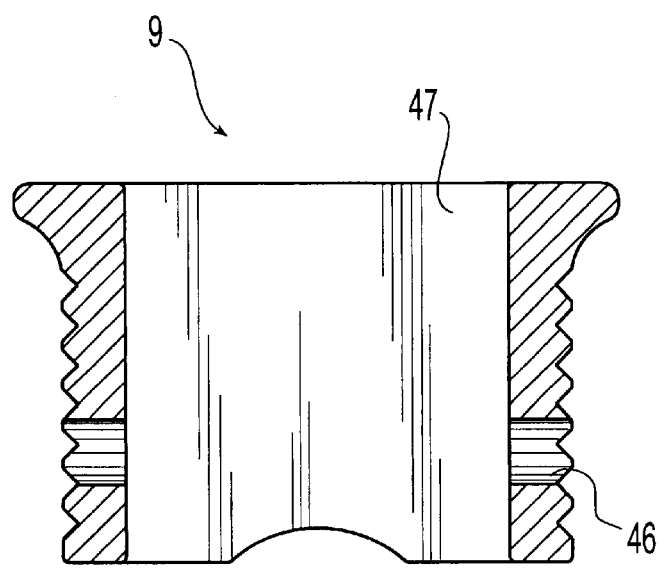
FIG. 2G is a top cross-sectional view of the handle lock assembly of the handle of FIG. 1.

Referring to FIG. 1 and best seen in FIGS. 2F & 2G, a sliding handle release 9 is provided in the preferred embodiment shown which is U-shaped and wraps around the bottom of the handle lock assembly body 7. Handle release 9 has a base 47 with sidewalls 48 projecting upwards and connected to the base. In one embodiment shown, handle release 9 has a flattened surface 45 which mates with and slides on a flat landing 44 (FIG. 2B) formed or machined on the body 7 of the handle lock assembly 2. Handle release 9 may be attached to each side of the handle slider 6 through windows 28 in the body 7 in any number of ways commonly used in the art. For example, the handle release 9 may be attached to the handle slider 6 with press-fit dowel pegs 10 as shown or with set screws (not shown) which fit into recesses 41 provided in the handle slider 6 (FIG. 2D) and pass through openings 46 in each side of the handle release 9. Preferably, the handle release 9 also has a ribbed or other nonslip surface 50 which will allow the surgeon to securely grip the release. A flange 51 also may be provided to assist gripping and retracting handle release 9. Although handle release 9 is depicted as U-shaped, the handle release is not limited to this embodiment and any shape or number of handle releases may be employed, the shape and number being a matter of ergonomic and/or design preference.

The handle lock assembly body 7 of handle lock assembly 2 may further contain an opening 8, preferably circular as depicted, extending completely through the body from the top 11 to the bottom 12 (FIGS. 2A and 2C). Retractable slider pin 5 protrudes into opening 8 in the body 7 through a side window 13 formed or cut into the side of the opening (best seen in FIG. 2C). This position is referred to as the "extended" position of the retractable slider pin 5.

As shown in FIG. 2C, the body 7 of the handle lock assembly 2 in one embodiment contains a transition portion 4 as discussed above and a handle attachment end 15 for connecting the handle lock assembly 2 to the grasping portion 3 (see also FIG. 1). Preferably, the attachment end 15 may be configured for welding to the grasping portion 3 as depicted, but is not limited in that regard. Thus, the handle lock assembly 2 may be connected to grasping portion 3 in any suitable manner commonly known in the art including semi-permanent connections such as threading the lock assembly to the handle grasping portion, the use of screws, fasteners, etc. Preferably, the attachment end 15 comprises a tapered cylindrical end designed to be inserted into a hollow handle grasping portion 3 which may be permanently connected to the handle lock assembly 2 by welding. As explained above, the handle lock assembly 2 may be designed with a minimal or no transition portion 4 of any type, the transition portion being strictly a matter of design choice. Moreover, enumerable possible shapes for the body 7 of handle lock assembly 2 and accompanying means of attaching the body to the grasping portion 3 are possible as will be evident without departing from the invention described herein; the shape and attachment means being a matter of design choice.

As shown in FIG. 2A, the gripping portion 3 may be angularly displaced from the plane of top 11 of the handle lock assembly body 7 as measured by an angle θ between the top 11 and a longitudinal centerline axis X—X drawn through the transition portion 4 (see FIG. 2B). Angle θ is preferably 0 degrees to 90 degrees, most preferably about 30 degrees. However, it will be readily apparent that angle θ may be varied to whatever angle is desired and necessary depending upon the particular intended surgical application and the configuration of the body 7, transition portion 4, and grasping portion 3 of the handle 1.

In one embodiment shown in FIGS. 2A and 2B, biasing members, which in this embodiment comprise springs 14, are provided within the handle lock assembly body 7 to hold the handle slider with retractable slider pin 5 in the "extended" position wherein the pin protrudes into the circular opening 8. The springs 14 may be confined on one end within recesses 15 (best seen in FIG. 2D) made in the handle slider 6. The other end of the springs 14 may contact the interior wall of the handle lock assembly body 7 located opposite the recesses 15.

The surgeon operates the handle lock assembly 2 by moving the handle release 9 in a direction which retracts the pin 5 from the circular opening 8 against the force of the springs 14. This position is referred to as the "retracted" position of the retractable slider pin 5. When the surgeon releases the handle release 9, the retractable slider pin 5 is automatically returned to its initial "extended" position (i.e., protruding into circular opening 8) by the springs 14. It will be appreciated that the present invention may be constructed with other forms of biasing members and with only one spring or any number of springs, the number and type of biasing members being strictly a matter of design choice.

Although helical springs are depicted, it will further be appreciated by those skilled in the art that the invention is not limited with regard to the style, size, or spring force constant (k) of the spring or springs that are used which will depend on the particular intended application. For example, leaf springs, torsion springs, cantilevered bending members, and other biasing members may be used. A spring force (k) should be selected which is sufficient to positively hold the retractable slider pin 5 in the "extended" position described above (i.e., the pin extending into the circular opening 8) to securely hold the cannula or other surgical instrument in the handle, while at the same time not being so great that it would be unduly difficult for the surgeon to retract the pin to the "retracted" position for changing or rotating the cannula or other surgical instrument. The springs 14 may be made of any suitable material commonly used for such members, and for the intended application of the device shown should be suitable for a surgical device. It should also be noted that the design of the recesses 15 provided in the handle slider 6 may be varied in any number of ways to accommodate the specific number, size, and style of biasing members employed. Alternatively, the springs 14 may engaged with the handle slider 6 or body 7 by other means commonly known in the art with and without the use of any recesses 15 whatsoever. For example, the body 7 may contain the recesses or other means to hold the springs 14.

Figure 3A:
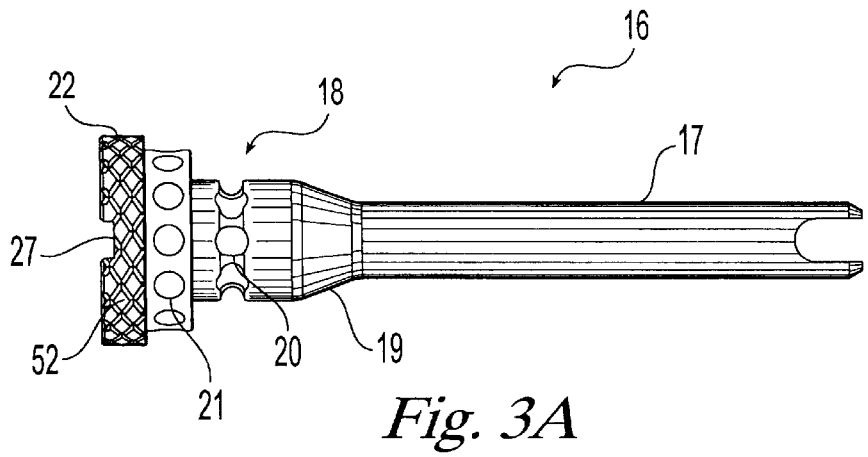
FIG. 3A is a plan view of a cannula which may be used interchangeably with the handle 1 of FIG. 1.
Figure 3B:
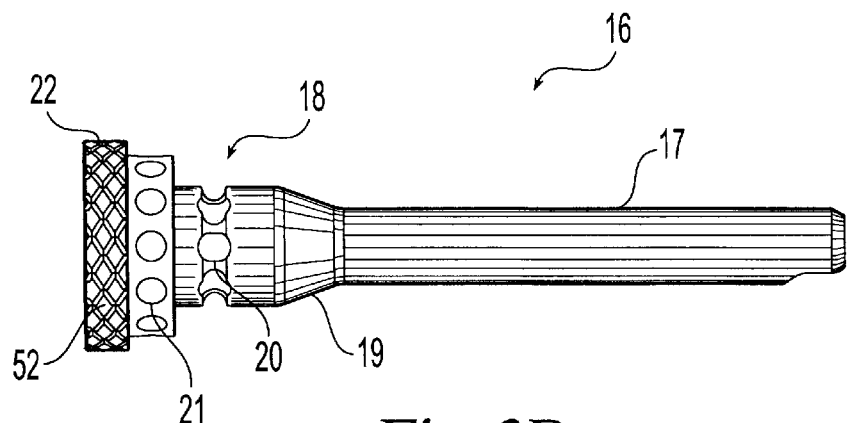
FIG. 3B is a 90 degree rotated plan view of the cannula of FIG. 3A.

The operation of the handle will be further understood by reference to FIGS. 3A and 3B which depict a cannula that may be used with the invention. Cannula 16 is a hollow tube-like structure that has a circular cross section comprising a body portion 17 and a head portion 18. In one embodiment, an inclined ramp portion 19 is provided which transitions the preferably smaller diameter body portion 17 to the larger diameter head portion 18. The shape of the ramp portion 19 causes the retractable slider pin 5 to automatically retract when the surgeon pushes the cannula 16 through the circular opening 8 of the handle lock assembly 2, the body portion 17 of the cannula being inserted first through the circular opening 8. This conveniently allows the cannula 16 to be inserted into the handle lock assembly 2 without the surgeon having to use the handle release 9. However, it should be noted that no ramp portion 19 is necessary with the present invention which is not limited in that regard. Accordingly, the body portion 17 and the head portion 18 may be of the same diameter and the surgeon would use the handle release 9 to insert the cannula 16 into the handle lock assembly 2, as explained more fully below, and then release the handle release to lock the cannula into position.

Still referring to FIGS. 3A and 3B, the cannula, or other surgical instrument designed to be used with the handle 1 may be provided with locking indentations 20. The indentations 20 may be provided around the circumference of the head portion 18 as shown to mate with the retractable slider pin 5 of the handle lock assembly (FIG. 2A). The shape and size of the locking indentations 20 may vary and are configured to mate with the retractable slider pin 5. In operation, the retractable slider pin 5 engages one of the locking indentations 20 when the cannula 16 is in position after it has been inserted through the circular opening 8 of the handle lock assembly 2 (FIG. 2A). Preferably, the retractable slider pin 5 mates with the indentations 20 in a manner so that the cannula 16 is positively locked in the handle 1 and cannot be inadvertently dislodged or withdrawn. Preferably, in order to remove or rotate the cannula, or other surgical instruments that may be used, the surgeon takes the positive step of using the handle release 9 to first retract the retractable slider pin 5. A knob 22 is formed on the end of head portion 18 of the cannula 16 and provides a structure for the surgeon to grasp while inserting or rotating the cannula. Preferably, the knob 22 has a knurled or similar non-slip surface 52.

Operation of the handle 1 of the present invention is best described by reference to FIGS. 2A, 2B, and 3A. The surgeon first selects the proper size cannula 16 for the particular surgical procedure involved. Cannula 16 having ramp portion 19 is inserted in the circular opening 8 in the handle lock assembly 2 of handle 1 until the retractable slider pin 5 engages one of the locking indentations 20 of the cannula, there by locking the cannula in the handle. In this scenario, the ramp portion 19 causes pin 5 to automatically retract as described above by inserting the cannula into the handle 1. Alternatively, if a cannula 16 is used that does not have a ramp portion 19 (i.e., the diameter of the cannula body portion 17 equals the diameter of the head portion 18), the surgeon preferably first moves the sliding handle release 9 to retract pin 5 before inserting the cannula in the handle 2. After the cannula 16 is inserted in the handle 1, handle release 9 is released by the surgeon so that pin 5 engages one of the locking indentations 20 thereby locking the cannula into the handle. This latter procedure of using the handle release 9 to retract pin 5 while inserting a cannula 16 may also be used with a cannula that has a ramp portion 19. Depending on the circumferential alignment of the retractable slider pin 5 with the locking indentations 20 when the cannula is inserted into the handle 1, it may be necessary to turn knob 22 on the head portion 18 of the cannula 16 to rotate the cannula until the pin and one indentation properly align and are engaged.

To remove cannula 16 from the handle 1, the surgeon moves the sliding handle release 9 to retract pin 5 and then withdraws the cannula. The handle release 9 may also be used in this same fashion to rotate a cannula 16 while it is inserted in the handle 1 if the surgeon prefers a different rotational position for the cannula.

Figure 4A:
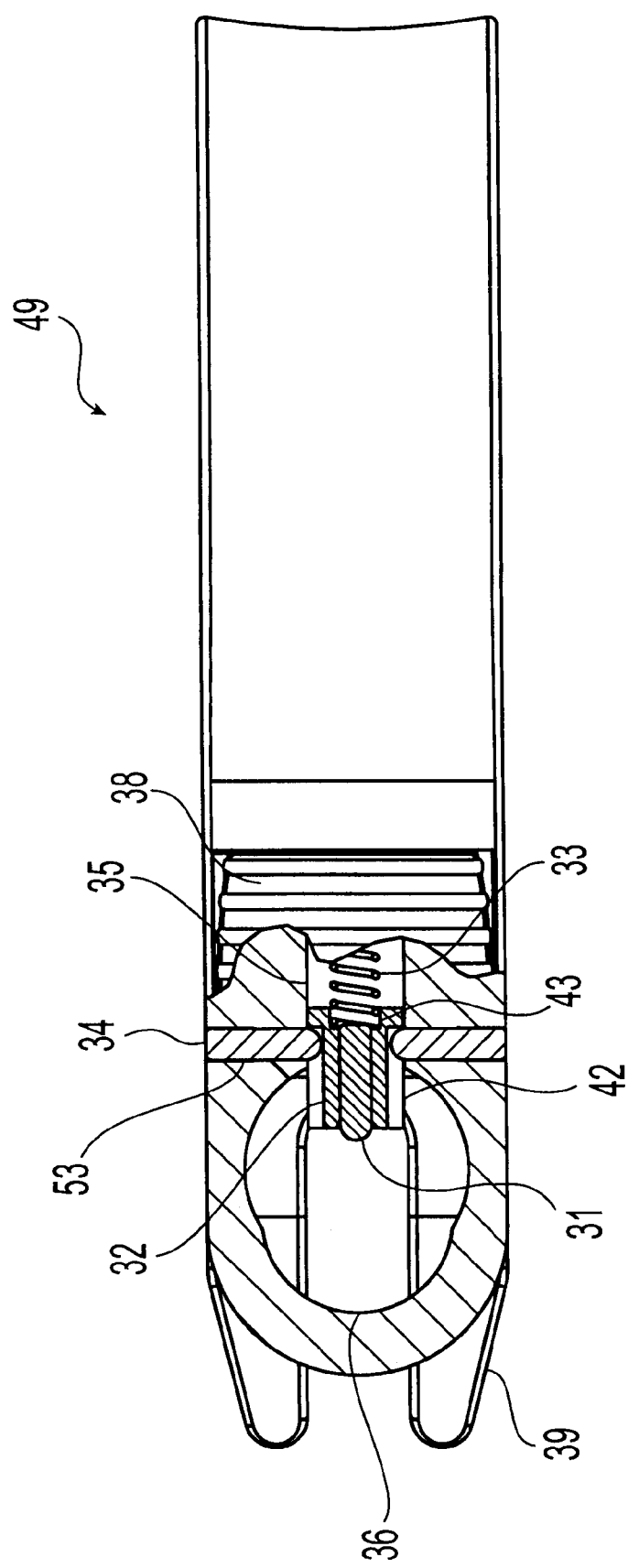
FIG. 4A is a top plan view of a soft tissue C-retractor which may be used with the handle of FIG. 1 shown with the sliding C-retractor releases partially removed.
Figure 4B:
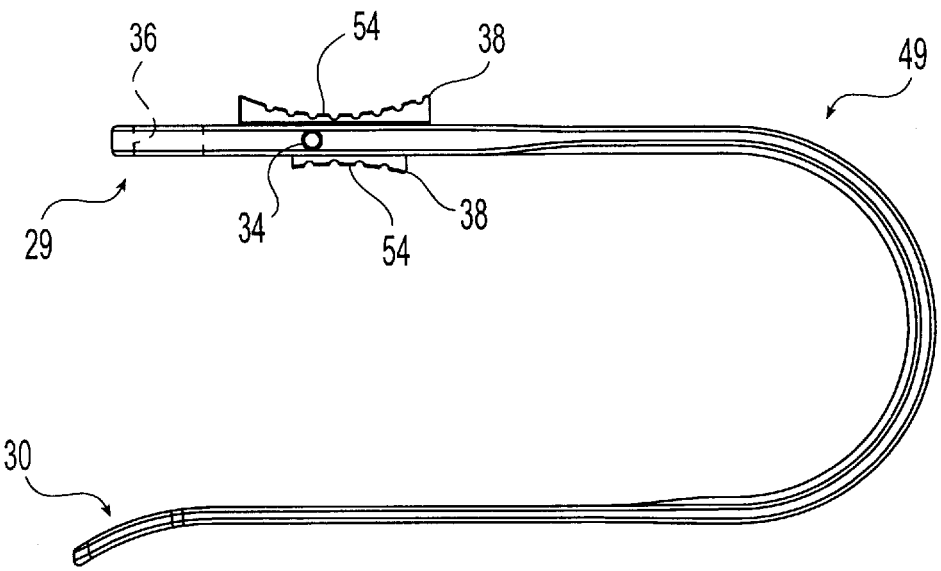
FIG. 4B is a side elevation view of a soft tissue C-retractor which may be used with the handle of FIG. 1.
Figure 4C:
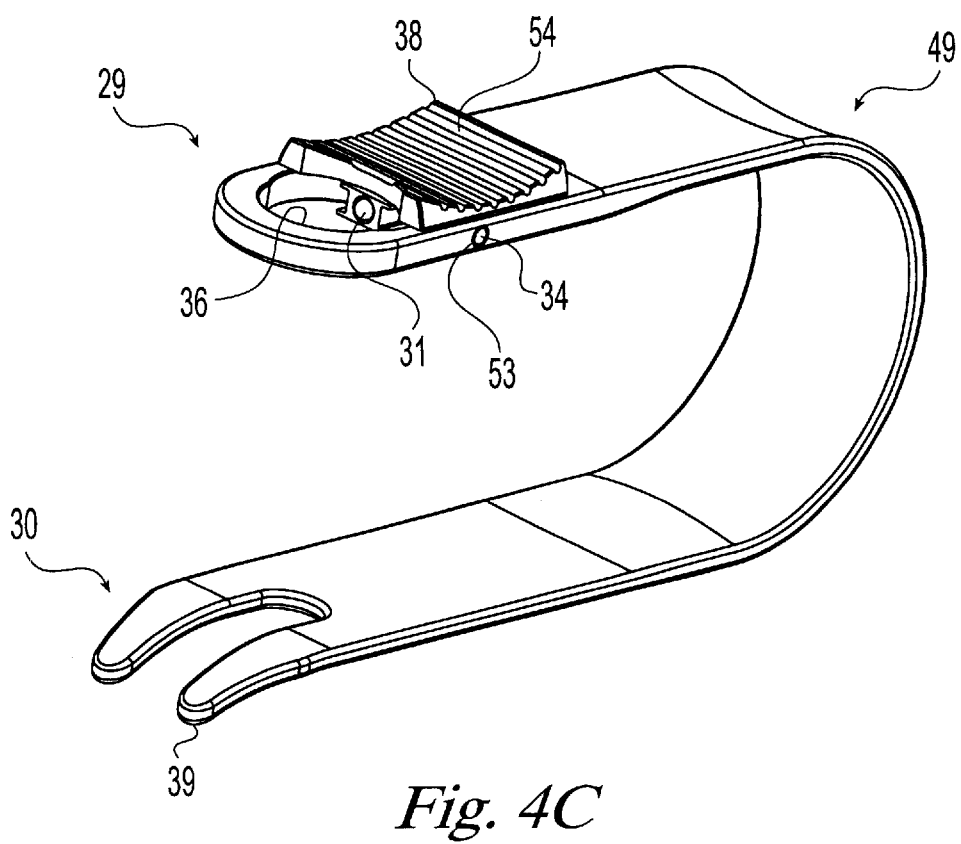
FIG. 4C is an isometric view of a soft tissue C-retractor which may be used with the handle of FIG. 1.

The cannula 16 in the embodiment shown in FIGS. 3A and 3B may preferably be provided with accessory depressions 21 which allow other surgical devices to be attached to the cannula which may utilize projections designed to mate with the depressions 21, thereby locking the devices to the cannula. One such device is a soft tissue retractor, such as cheek C-retractor 49 as shown in FIGS. 4A–4C, which is commonly used in maxillofacial surgery. The cheek retractor is often used for surgery involving the mandible or jawbone near the ear. In FIG. 4A, the cheek retractor 49 in one embodiment includes locking end portion 29 on one end of the C-retractor and a forked end portion 30 on the opposite end. Locking end portion 29 further comprises a retractable slider projection 31, a projection-carrying slider 32, at least one biasing member which preferably is a spring 33 as shown, and press-fit dowel pegs 34. An opening 36, preferably circular or oval, is also provided in locking end portion 29 along with an open keyway 35, preferably rectangular. Both opening 36 and keyway 35 extend completely through the locking portion 29. Also preferably, the open keyway 35 intersects the opening 36 to form a single contiguous opening wherein sits the retractable slider projection 31, projection-carrying slider 32, and spring 33. The projection 31 may be attached to the slider 32 in any manner commonly known in the art, and may in fact be an integral part of the slider formed during manufacture of the slider.

Still referring to FIGS. 4A–4C, the retractable slider projection 31 is held in an "extended" position by the spring 33 whereby the projection protrudes into opening 36. One end of spring 33 rests in a recess 43 provided in the rear of projection-carrying slider 32 while the other end of the spring contacts the back wall of keyway 35. The spring force of spring 33 should be selected to provide sufficient force to hold projection 31 into the "extended" position, while at the same time the force should not be so great that it would be unduly difficult for the surgeon to retract the projection. At least one groove or channel 42 may be provided in one or both sides of projection-carrying slider 32 which is closed at the rear near the spring 33. Press-fit dowel pegs 34 may be furnished which ride in the groove or grooves 42 and pass through openings 53 in the sides of the locking end portion 29. Alternatively, set screws or other means well known in the art may be used in lieu of dowel pegs 34. The dowel pegs 34 serve to hold the projection-carrying slider 32 in the locking end portion 29 of the C-retractor 49 by contacting the closed end of grooves 42 to prevent the spring 33 from pushing the projection-carrying slider into opening 36.

As best seen in FIGS. 4B and 4C, preferably two sliding C-retractor releases 38 may be provided for retracting slider projection 31 against the force of spring 33 to a "retracted" position whereby the projection is withdrawn from opening 36 into keyway 35. The retractor releases are attached to the top and bottom of projection-carrying slider 32 by an means commonly known in the art and may in fact be an integral part of the slider 32 formed during the manufacture of the slider. When the releases 38 are in place, the releases serve as a closure for the top and bottom of keyway 35. The retractor releases 38 preferably have a ribbed or other non-slip surface 54 which may be readily gripped by the surgeon. The retractor releases 38 may also be contoured and shaped to assist a surgeon in retracting the slider projection 31.

The forked end portion 30 of the C-retractor 49 includes two prongs 39; preferably, the prongs are curved away from the C-retractor 49 as shown. Alternatively, the shape of prongs 39 may be straight.

Use of the cheek C-retractor 49 can best be explained by reference to FIGS. 3A and 4A–4C. After the cannula 16 of handle 1 has been inserted through a patient's cheek, the forked end portion is inserted through a patient's mouth such that the body portion 17 of the cannula (inside the mouth) becomes situated between the two prongs 39. The locking end portion 29 is then affixed to the handle 1 (which is outside the patient's mouth) by using the sliding retractor releases 38 to retract projection 31, slipping opening 36 of the C-retractor 49 over knob 22 on the back of the cannula head portion 18 until the retractable slider projection 31 of the C-retractor aligns with one of the accessory depressions 21 of the cannula, and then releasing the releases 38 to engage the projection in one of the accessory depressions. The C-retractor is thereby secured to the handle 1. The slider projection 31 may also be retracted while the C-retractor 49 remains in position on the handle 1 in order to rotate the C-retractor to a number of positions around and in relation to the handle that may be desired by the surgeon.

Figure 5:
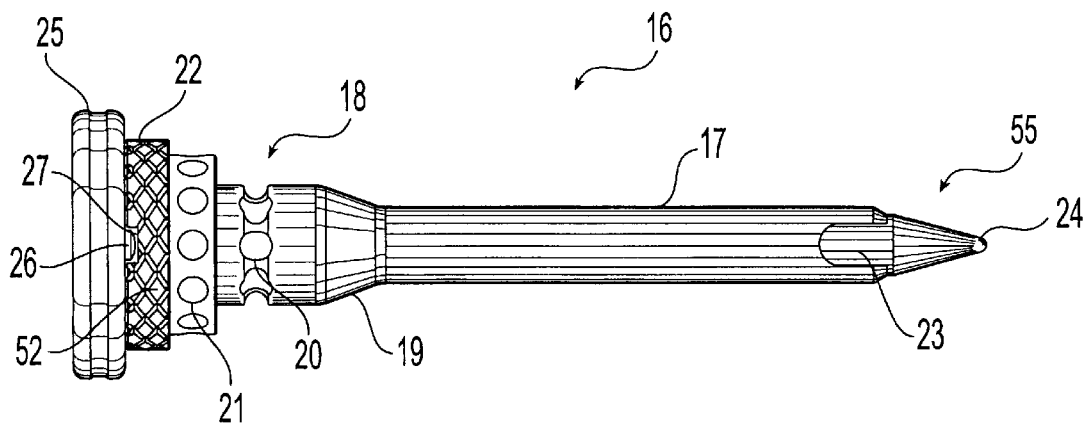
FIG. 5 illustrates the cannula of FIGS. 3A & 3B with an inserted obturator which may be used with the handle of FIG. 1.

Numerous surgical instruments can also be inserted and used through the cannula 16. Referring to FIG. 5, for example, an obturator 55 which is commonly used in minimially invasive surgical procedures is shown as being inserted in the cannula 16. The obturator in the embodiment depicted consists of a solid round shaft 23 (partially visible at the distal end of the cannula body portion 17) with a conically pointed tip 24 at one end and an enlarged, round head 25 at the opposite end. The shaft 23 is rigidly attached to head 25 in any manner commonly known in the art, such as by welding, set screws threaded attachment, etc. In the embodiment shown, the obturator head 25 has at least one tab 26 which is designed to mate with at least one slot 27 provided in the knob 22 of cannula 16. This prevents the obturator 55 from rotating once it has been inserted through the cannula 16. Drill guides (not shown) which are also commonly employed in surgery for fracture fixation may also be used with the cannula 16 of handle 1. These drill guides may be designed to be compatible for use with cannula 16 and may also include at least one tab on a enlarged, round head like the obturator 55 which mates with at least one slot 27 provided in the knob 22 of the cannula.

Figure 6:
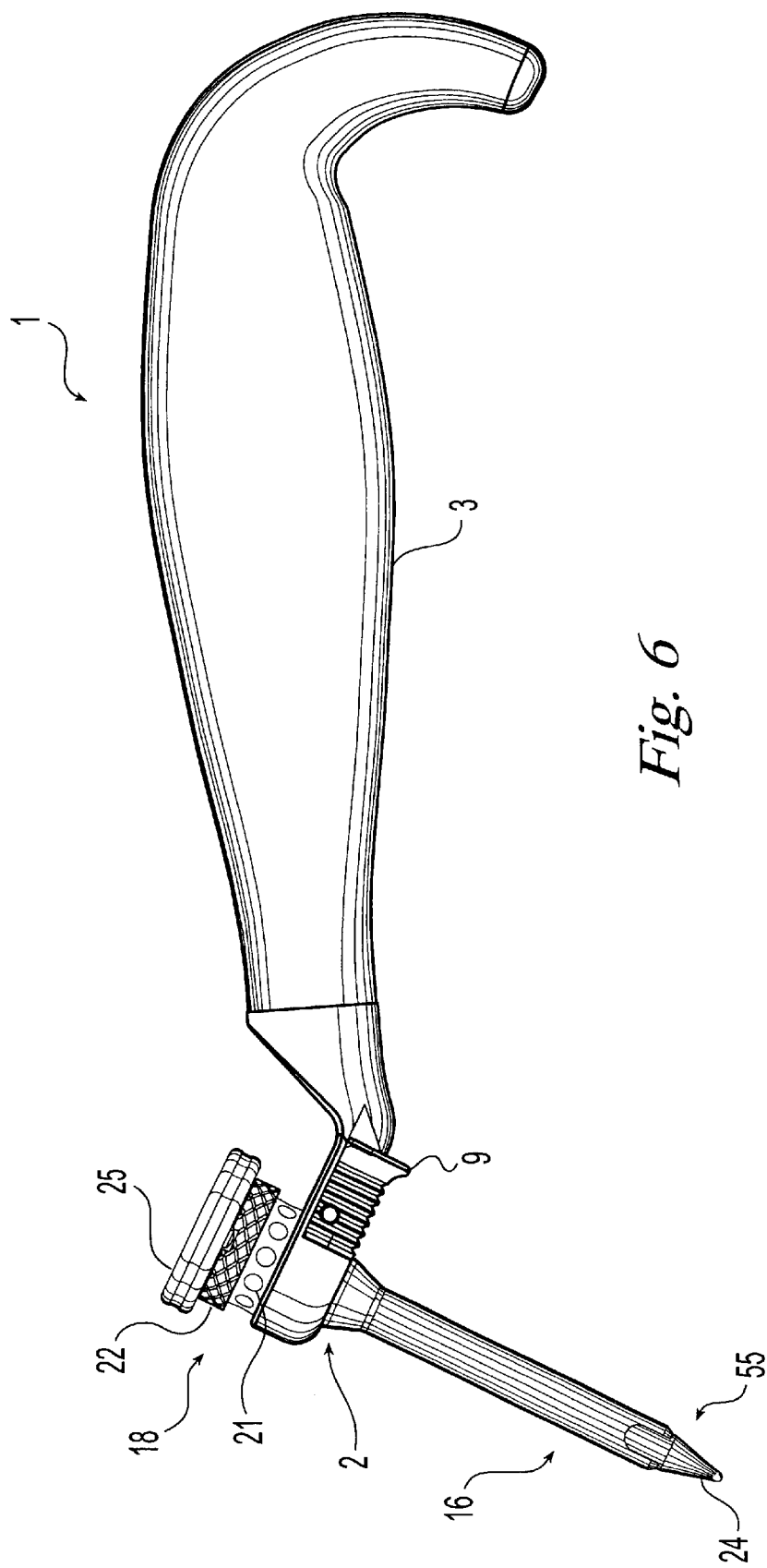
FIG. 6 is a side elevation view of the handle of FIG. 1 with an inserted cannula and obturator.

FIG. 6 depicts a fully assembled handle 1 with a cannula 16 inserted and locked in place by the handle lock assembly 2. An obturator 55 is shown inserted in the handle 1 with its pointed tip 24 protruding from the end of the cannula 16 and the obturator's enlarged, round head 25 visible at the opposite end of the cannula.

The handle including all of the forgoing components described (i.e., the cannula, obturator, drill guides, C-retractor, etc.) may be constructed of any material suitable for use in surgical procedures. For example, the handle and its components may preferably be made of stainless steel which is commonly used; however, the invention is not limited in the type of materials employed which would be a matter of design choice.

It will be appreciated by those skilled in the art that the details of the handle described herein are a matter of design choice, and that the invention is not limited to the particular embodiments or those features described. Accordingly, numerous modifications may be made to the handle and its components without departing from the spirit of the invention and scope of the claims appended hereto.

What is claimed is:

1. A system for performing a surgical procedure comprising:
   a handle having a grasping portion and a handle lock assembly, the lock assembly having a body with a top and a bottom, and a retractable slider pin; and
   a cannula having indentations to engage the retractable slider pin.

2. The system of claim 1 wherein the cannula further comprises depressions for securing at least one additional surgical device to the handle.

3. The system of claim 2 further comprising a soft tissue retractor engaged with at least one of the depressions of the cannula.

4. The system of claim 1 wherein the cannula has a body portion and a head portion, the body and head portions being of different diameters in size.

5. The system of claims 4 wherein the cannula has an inclined ramp between the body portion and head portion.

6. The system of claim 1 further comprising a knob connected to the cannula for grasping and rotating the cannula.

7. The system of claim 6 further comprising at least one slot in the knob for mating with and engaging at least one tab provided on a surgical instrument to be inserted through the cannula to prevent rotation of the surgical instrument while in the cannula.

8. The system of claim 7 wherein the surgical instrument with the at least one tab is an obturator.

9. The system of claim 7 wherein the surgical instrument with the at least one tab is a drill guide.

10. The system of claim 1 wherein the handle lock assembly includes an opening disposed in the body extending from the top to the bottom for inserting the cannula, the retractable slider pin being movable from an extended position in which the pin protrudes into the opening and engages with the indentations of the cannula to a retracted position in which the pin is withdrawn from the indentations.

11. The system of claim 1, further comprising the cannula having a circumference, and the indentations being arranged around the circumference of the cannula.

12. The system of claim 11, wherein the indentations are approximately circular when viewed from the top.

13. A handle for releaseably attaching at least one surgical instrument comprising:
   a grasping portion; and
   a handle lock assembly having a body with a top and a bottom, a retractable slider pin for securing a surgical instrument to the handle, and a handle slider connected to the slider pin;

wherein the lock assembly body includes an opening disposed in the body for inserting surgical instruments, the opening extending from the top to the bottom of the body, the retractable slider pin being movable from an extended position in which the pin protrudes into the opening to a retracted position in which the pin is withdrawn from the opening.

14. The handle of claim 13 further comprising at least one handle release operatively connected to the slider pin for moving the retractable slider pin from the extended position to the retracted position.

15. The handle of claim 13 wherein the lock assembly further comprises at least one biasing member for biasing the retractable slider pin toward the extended position.

16. The handle of claim 15 wherein the at least one biasing member is a helical spring.

17. The handle of claim 13 wherein the handle slider further comprises a recess for holding at least one biasing member.

18. The handle of claim 13 wherein the lock assembly is attached to the grasping portion by welding.

19. The handle of claim 13 wherein the grasping portion is hollow.

20. The handle of claim 13 further comprising at least one surgical instrument having indentations to engage the retractable slider pin.

21. The handle of claim 13 wherein the opening is circular.

22. The handle of claim 13 wherein the body further comprises a transition portion between the handle lock assembly and the grasping portion.

23. The handle of claim 13 wherein the grasping portion is angularly displaced from the plane of the top of the body.

24. The handle of claim 23 wherein the angular displacement is about 30 degrees.

25. The handle of claim 13 wherein the retractable slider pin is movable by manipulating at least one handle release operatively engaged with the handle slider.

26. A handle for releaseably securing at least one surgical instrument, the handle comprising:
   a grasping portion; and
   an adjacent handle lock assembly comprising:
   a body having a top, a bottom, and an opening for inserting a surgical instrument therethrough extending from the top to the bottom of the body;
   a handle slider between the top and bottom of the body, the handle slider including at least two substantially planar surfaces oriented substantially parallel to each other;
   a pin for securing the surgical instrument to the handle, the pin attached to the handle slider and pointed towards the opening;
   wherein the pin is moveable between an extended position in which the pin protrudes into the opening and a retracted position in which the pin is withdrawn from the opening.

27. The handle of claim 26, further comprising at least one handle release operatively engaged with the handle slider for moving the pin between the extended and retracted positions.

28. The handle of claim 27, wherein the handle release is slidably disposed on the bottom of the handle lock assembly body.

29. The handle of claim 28, wherein the handle release is substantially U-shaped.

30. The handle of claim 28, wherein the bottom of the handle body has a substantially flat landing for slidably engaging the handle release.

31. The handle of claim 26, further comprising a cavity disposed in the body and the slider slidably disposed in the cavity, the cavity communicating with the opening in the body.

32. The handle of claim 31, wherein the cavity is wider than the opening.

33. The handle of claim 31, further comprising at least one handle release operatively engaged with the handle slider for moving the pin between the extended and retracted positions.

34. The handle of claim 33, further comprising at least one window disposed in the body, the window extending into the cavity from outside, the handle release attached to the slider through the window.

35. The handle of claim 34, wherein two windows are disposed in the body, the handle release attached to the slider at least through one window.

36. The handle of claim 33, wherein the handle release is substantially U-shaped.

37. The handle of claim 27, wherein the handle lock assembly further comprises at least one biasing member for biasing the retractable slider pin toward the extended position.

38. The handle of claim 37, wherein two biasing members are provided.

39. A system for performing a surgical procedure comprising:
   a handle-having a grasping portion and a handle lock assembly, the handle lock assembly having a body with a top and a bottom, a retractable slider pin for securing a surgical instrument to the handle, and a handle slider connected to the slider pin;
   wherein the lock assembly body includes an opening disposed in the body for inserting surgical instruments, the opening extending from the top to the bottom of the body, the retractable slider pin being movable from an extended position in which the pin protrudes into the opening to a retracted position in which the pin is withdrawn from the opening; and
   at least one surgical instrument associated with the handle and releaseably disengageable therefrom by moving the handle slider, the surgical instrument comprising a plurality of circumferentially-arranged indentations configured and adapted to engage the slider pin, wherein the surgical instrument is not axially movable when the slider pin is in the extended position.

40. The system of claim 39, wherein the surgical instrument can be rotated in the handle when the slider pin is in the retracted position without axially moving the surgical instrument.

41. The system of claim 40, wherein the surgical instrument is a cannula.

42. The system of claim 41, further comprising at least one handle release operatively connected to the handle slider for moving the retractable slider pin from the extended position to the retracted position.

43. The system of claim 41, wherein the cannula further comprises a plurality of depressions for securing at least one additional surgical device.

44. The system of claim 43, further comprising a soft tissue retractor engaged with at least one of the depressions of the cannula.

45. The system of claim 44, wherein the cannula has a body portion and a head portion, the body and head portions being of different diameters in size.

46. The system of claim 45, wherein the cannula has an inclined ramp between the body portion and head portion.

47. The system of claim 44, further comprising a knob connected to the cannula for grasping and rotating the cannula.

48. The system of claim 47, further comprising at least one slot in the knob for mating with and engaging at least one tab provided on an insertable surgical instrument to be inserted through the cannula to prevent rotation of the surgical instrument while in the cannula.

49. The system of claim 48, wherein the insertable surgical instrument with the at least one tab is an obturator.

50. The system of claim 48, wherein the insertable surgical instrument with the at least one tab is a drill guide.

51. A method of changing surgical instruments in a surgical procedure comprising:

(a) providing a handle, the handle having a grasping portion and a lock assembly, the lock assembly having a body with a top and a bottom, a retractable slider pin for securing a surgical instrument to the handle, and a handle slider connected to the slider pin, the handle slider including at least two substantially planar surfaces oriented substantially parallel to each other;

wherein the lock assembly body includes an opening disposed in the body for inserting surgical instruments, the opening extending from the top to the bottom of the body, the retractable slider pin being movable from an extended position in which the pin protrudes into the opening to a retracted position in which the pin is withdrawn from the opening;

(b) retracting the retractable pin from the extended position to the retracted position in the lock assembly whereby the pin is withdrawn from the passageway; and (c) removing a first surgical instrument from the handle.

52. The method of claim 51 further comprising inserting a second different instrument having indentations configured and adapted to engage the retractable slider pin into the passageway of the handle.

53. The method of claim 52 wherein at least one of the surgical instruments is a cannula having indentations configured and adapted to mate with the slider pin to secure the cannula to the handle.

54. The method of claim 52 further comprising locking the second instrument to the handle by engaging the retractable pin in one of the indentations.

55. The method of claim 54 further comprising rotating the second different instrument to align the indentations and slider pin before engaging the retractable pin in one of the indentations.

56. The method of claim 51 further comprising withdrawing the slider pin from the passageway to the retracted position by a user and inserting a second different instrument having indentations configured and adapted to engage the retractable slider pin through the passageway before engaging the slider pin in one of the indentations in the second instrument.

57. The method of claim 51 further comprising:

providing a second different surgical instrument having indentations configured and adapted to engage the retractable slider pin;

inserting the second instrument in the handle;

locking the second instrument to the handle by engaging the retractable pin in one of the indentations;

retracting the retractable pin from the extended position to the retracted position in the lock assembly whereby the pin is withdrawn from the passageway; and removing the second instrument from the handle.

58. The method of claim 57 further comprising withdrawing the slider pin from the passageway to the retracted position by a user and inserting the second surgical instrument through the passageway before the slider pin engages one of the indentations in the second surgical instrument to lock the second surgical instrument to the handle.

59. The method of claim 57 further comprising rotating the second surgical instrument to align the indentations and sliding pin before engaging the retractable pin in one of the indentations.

\* \* \* \* \*

UNITED STATES PATENT AND TRADEMARK OFFICE
CERTIFICATE OF CORRECTION

PATENT NO.   : 6,524,238 B2
DATED        : April 14, 2003
INVENTOR(S)  : James Velikaris and Sean Kerr It is certified that error appears in the above-identified patent and that said Letters Patent is hereby corrected as shown below:

Column 11,
Line 1, after "slider" add -- disposed in the body and --;

Column 12,
Line 30, delete "-" between "handle" and "having";
Line 65, replace "44" with -- 41 --;

Column 13,
Line 3, replace "44" with -- 41 --; and
Line 21, after "slider" add -- disposed in the body and --. (first occurrence)

Signed and Sealed this

Fifth Day of August, 2003

JAMES E. ROGAN
*Director of the United States Patent and Trademark Office*